United States Patent
Zhu et al.

(10) Patent No.: US 11,767,524 B2
(45) Date of Patent: Sep. 26, 2023

(54) HIS-MBP TAGGED DNA ENDONUCLEASE FOR FACILITATED ENZYME REMOVAL

(71) Applicant: ABclonal Science Inc., Woburn, MA (US)

(72) Inventors: Zhenyu Zhu, Lynnfield, MA (US); Dapeng Sun, Lexington, MA (US); Michaela Shottes, Methuen, MA (US)

(73) Assignee: ABclonal Science, Inc., Woburn, MA (US)

( * ) Notice: Subject to any disclaimer, the term of this patent is extended or adjusted under 35 U.S.C. 154(b) by 635 days.

(21) Appl. No.: 17/027,747

(22) Filed: Sep. 22, 2020

(65) Prior Publication Data
US 2021/0087550 A1    Mar. 25, 2021

Related U.S. Application Data

(60) Provisional application No. 62/904,866, filed on Sep. 24, 2019.

(51) Int. Cl.
*C12N 15/10* (2006.01)
*C12N 9/22* (2006.01)

(52) U.S. Cl.
CPC .......... *C12N 15/1013* (2013.01); *C12N 9/22* (2013.01); *C12N 15/102* (2013.01); *C12N 15/1065* (2013.01); *C07K 2319/00* (2013.01)

(58) Field of Classification Search
None
See application file for complete search history.

(56) References Cited

U.S. PATENT DOCUMENTS

2009/0092582 A1 * 4/2009 Bogin ...................... A61P 3/10
435/69.51

* cited by examiner

*Primary Examiner* — Suzanne M Noakes
*Assistant Examiner* — Jae W Lee
(74) *Attorney, Agent, or Firm* — Eric P. Mirabel

(57) ABSTRACT

Disclosed is a product and process, wherein one adds a N-terminal Histamine-Maltose Binding Protein ("MBP") tag to endonucleases, including restriction endonucleases like Hind III, and binds the tagged fusion protein to a solid support, preferably beads, once the enzyme has digested oligonucleotides in solution, in order to arrest further digestion. Preferred beads for binding the tagged enzyme are magnetic beads, which can easily be removed from solution by binding to a support and then removing it, or can be accumulated by magnetic attraction in a particular region. More preferred are magnetic beads bound to iminodiacetic acid or nitrilotriacetic acid.

14 Claims, 2 Drawing Sheets
Specification includes a Sequence Listing.

Fig. 1

HindIII-HM Activity on Lambda DNA Before (lanes 1-12) and After (lanes 13-24) Enzyme Removal

Fig. 2

HindIII-HM Activity Before and After Enzyme Removal by Bead Adsorption

SEQUENCE LISTING

```
<160> NUMBER OF SEQ ID NOS: 3

<210> SEQ ID NO 1
<211> LENGTH: 2079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaaaatcc accaccacca ccaccacgaa gaaggtaaac tggttatctg gatcaacggt        60
gacaaaggtt acaacggtct ggcggaagtt ggtaaaaaat tcgaaaaaga caccggtatc       120
aaagttaccg ttgaacaccc ggacaaactg gaagaaaaat tcccgcaggt tgcggcgacc       180
ggtgacggtc cggacatcat cttctgggcg cacgaccgtt tcggtggtta cgcgcagtct       240
ggtctgctgg cggaaatcac cccggacaaa gcgttccagg acaaactgta cccgttcacc       300
tgggacgcgg ttcgttacaa cggtaaactg atcgcgtacc cgatcgcggt tgaagcgctg       360
tctctgatct acaacaaaga cctgctgccg aacccgccga aacctggga agaaatcccg        420 gcgctggaca agaactgaa agcgaaaggt aaatctgcgc tgatgttcaa cctgcaggaa        480
ccgtacttca cctggccgct gatcgcggcg gacggtggtt acgcgttcaa atacggtgac       540
atcaaagacg ttggtgttga caacgcgggt gcgaaagcgg gtctgacctt cctggttgac       600
ctgatcaaaa acaaacacat gaacgcggac accgactact ctatcgcgga agcggcgttc       660
aacaaaggtg aaaccgcgat gaccatcaac ggtccgtggg cgtggtctaa catcgacacc       720
tctaaagtta actacggtgt taccgttctg ccgaccttca aggtcagcc gtctaaaccg        780 ttcgttggtg ttctgtctgc gggtatcaac gcggcgtctc cgaacaaaga actggcgaaa       840
gaattcctgg aaaaactacct gctgaccgac gaaggtctgg aagcggttaa caaagacaaa       900
ccgctgggtg cggttgcgct gaaatcttac gaagaagaac tggcgaaaga cccgcgtatc       960
gcggcgaccg cggaaaacgc ggcgaaaggt gaaatcatgc cgaacatccc gcagatgtct      1020
gcgttctggt acgcggttcg taccgcggtt atcaacgcgg cgtctggtcg tcagaccgtt      1080
gacgaagcgc tgaaagacgc gcagaccaac tcttcttcta caataataa caataacaat      1140 aacaacaacc tgggtgaaaa cctgtacttc cagggtatga aaaatcagc cttagaaaaa      1200 ctgctgtctc tgatcgaaaa tctgaccaat caagagttta acaggctac aatagtctg       1260 attagcttta tctacaagct gaatcgtaat gaggtcatcg aactggttcg cagcatcggc      1320
atcctgccgg aagctatcaa accgtctagt acccaggaaa aactgtttag caaagcgggc      1380
gatattgtgc tggccaaagc ctttcagtta ctgaatctga atagcaaacc tctggaacag      1440
cgtggtaatg caggcgatgt gattgccctg tctaaagagt tcaattatgg cttagttgcg      1500
gatgccaaat catttcgcct gtcacgcacg gctaaaaatc agaaagattt taaagttaaa      1560
gcgttaagtg aatggcgcga agataaagat tatgcggtgc tgaccgcacc gttttttccag     1620 tatccgacga ccaaatctca gatttttaaa cagtcattag atgaaaatgt gttactgttt      1680
tcatgggaac atcggccat cctgctacaa ctggatctga agaaaccaa tatctttccg        1740 tttgaacagc tgtggaattt tcctaaaaaa cagtctaaga aaacgagtgt gagcgatgcc      1800
gaaaacaatt ttatgcgcga ttttaataag tattttatgg atctgtttaa aattgataaa      1860
gatacgctga atcagttact gcaaaaagaa atcaatttta tcgaagaacg ctcactgatt      1920
```

```
gaaaaagaat attggaaaaa acagatcaat attatcaaaa attttacacg cgaagaagcc    1980
atcgaagcct tactgaaaga tattaatatg agtagcaaaa tcgaaaccat tgatagcttt    2040
atcaaaggca tcaaatctaa tgatcgcctg tatctgtaa                           2079
```

<210> SEQ ID NO 2
<211> LENGTH: 692
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Lys Ile His His His His His His Glu Glu Gly Lys Leu Val Ile
1               5                   10                  15

Trp Ile Asn Gly Asp Lys Gly Tyr Asn Gly Leu Ala Glu Val Gly Lys
            20                  25                  30

Lys Phe Glu Lys Asp Thr Gly Ile Lys Val Thr Val Glu His Pro Asp
        35                  40                  45

Lys Leu Glu Glu Lys Phe Pro Gln Val Ala Ala Thr Gly Asp Gly Pro
    50                  55                  60

Asp Ile Ile Phe Trp Ala His Asp Arg Phe Gly Gly Tyr Ala Gln Ser
65                  70                  75                  80

Gly Leu Leu Ala Glu Ile Thr Pro Asp Lys Ala Phe Gln Asp Lys Leu
                85                  90                  95

Tyr Pro Phe Thr Trp Asp Ala Val Arg Tyr Asn Gly Lys Leu Ile Ala
            100                 105                 110

Tyr Pro Ile Ala Val Glu Ala Leu Ser Leu Ile Tyr Asn Lys Asp Leu
        115                 120                 125

Leu Pro Asn Pro Pro Lys Thr Trp Glu Glu Ile Pro Ala Leu Asp Lys
    130                 135                 140

Glu Leu Lys Ala Lys Gly Lys Ser Ala Leu Met Phe Asn Leu Gln Glu
145                 150                 155                 160

Pro Tyr Phe Thr Trp Pro Leu Ile Ala Ala Asp Gly Gly Tyr Ala Phe
                165                 170                 175

Lys Tyr Gly Asp Ile Lys Asp Val Gly Val Asp Asn Ala Gly Ala Lys
            180                 185                 190

Ala Gly Leu Thr Phe Leu Val Asp Leu Ile Lys Asn Lys His Met Asn
        195                 200                 205

Ala Asp Thr Asp Tyr Ser Ile Ala Glu Ala Ala Phe Asn Lys Gly Glu
    210                 215                 220

Thr Ala Met Thr Ile Asn Gly Pro Trp Ala Trp Ser Asn Ile Asp Thr
225                 230                 235                 240

Ser Lys Val Asn Tyr Gly Val Thr Val Leu Pro Thr Phe Lys Gly Gln
                245                 250                 255

Pro Ser Lys Pro Phe Val Gly Val Leu Ser Ala Gly Ile Asn Ala Ala
            260                 265                 270

Ser Pro Asn Lys Glu Leu Ala Lys Glu Phe Leu Glu Asn Tyr Leu Leu
        275                 280                 285

Thr Asp Glu Gly Leu Glu Ala Val Asn Lys Asp Lys Pro Leu Gly Ala
    290                 295                 300

Val Ala Leu Lys Ser Tyr Glu Glu Glu Leu Ala Lys Asp Pro Arg Ile
305                 310                 315                 320

Ala Ala Thr Ala Glu Asn Ala Ala Lys Gly Glu Ile Met Pro Asn Ile
                325                 330                 335
```

```
Pro Gln Met Ser Ala Phe Trp Tyr Ala Val Arg Thr Ala Val Ile Asn
            340                 345                 350

Ala Ala Ser Gly Arg Gln Thr Val Asp Glu Ala Leu Lys Asp Ala Gln
            355                 360                 365

Thr Asn Ser Ser Ser Asn Asn Asn Asn Asn Asn Asn Asn Asn Asn Leu
            370                 375                 380

Gly Glu Asn Leu Tyr Phe Gln Gly Met Lys Lys Ser Ala Leu Glu Lys
385                 390                 395                 400

Leu Leu Ser Leu Ile Glu Asn Leu Thr Asn Gln Glu Phe Lys Gln Ala
                405                 410                 415

Thr Asn Ser Leu Ile Ser Phe Ile Tyr Lys Leu Asn Arg Asn Glu Val
            420                 425                 430

Ile Glu Leu Val Arg Ser Ile Gly Ile Leu Pro Glu Ala Ile Lys Pro
            435                 440                 445

Ser Ser Thr Gln Glu Lys Leu Phe Ser Lys Ala Gly Asp Ile Val Leu
            450                 455                 460

Ala Lys Ala Phe Gln Leu Leu Asn Leu Asn Ser Lys Pro Leu Glu Gln
465                 470                 475                 480

Arg Gly Asn Ala Gly Asp Val Ile Ala Leu Ser Lys Glu Phe Asn Tyr
                485                 490                 495

Gly Leu Val Ala Asp Ala Lys Ser Phe Arg Leu Ser Arg Thr Ala Lys
            500                 505                 510

Asn Gln Lys Asp Phe Lys Val Lys Ala Leu Ser Glu Trp Arg Glu Asp
            515                 520                 525

Lys Asp Tyr Ala Val Leu Thr Ala Pro Phe Phe Gln Tyr Pro Thr Thr
            530                 535                 540

Lys Ser Gln Ile Phe Lys Gln Ser Leu Asp Glu Asn Val Leu Leu Phe
545                 550                 555                 560

Ser Trp Glu His Leu Ala Ile Leu Leu Gln Leu Asp Leu Glu Thr
                565                 570                 575

Asn Ile Phe Pro Phe Glu Gln Leu Trp Asn Phe Pro Lys Lys Gln Ser
            580                 585                 590

Lys Lys Thr Ser Val Ser Asp Ala Glu Asn Asn Phe Met Arg Asp Phe
            595                 600                 605

Asn Lys Tyr Phe Met Asp Leu Phe Lys Ile Asp Lys Asp Thr Leu Asn
            610                 615                 620

Gln Leu Leu Gln Lys Glu Ile Asn Phe Ile Glu Glu Arg Ser Leu Ile
625                 630                 635                 640

Glu Lys Glu Tyr Trp Lys Lys Gln Ile Asn Ile Ile Lys Asn Phe Thr
                645                 650                 655

Arg Glu Glu Ala Ile Glu Ala Leu Leu Lys Asp Ile Asn Met Ser Ser
            660                 665                 670

Lys Ile Glu Thr Ile Asp Ser Phe Ile Lys Gly Ile Lys Ser Asn Asp
            675                 680                 685

Arg Leu Tyr Leu
    690

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Met Lys Ile His His His His His
1               5
```

HIS-MBP TAGGED DNA ENDONUCLEASE FOR FACILITATED ENZYME REMOVAL

SEQUENCE LISTING

The instant application contains a Sequence Listing which has been submitted electronically in ASCII format and is hereby incorporated by reference in its entirety. Said ASCII copy, created on Sep. 21, 2020, is named ABCL-HindIII_S-L.txt and is 9,421 bytes in size.

BACKGROUND

DNA endonucleases digest DNA and restriction endonucleases digest DNA at particular sequences. If a reaction with a DNA oligomer is to be performed after endonuclease digestion, the endonuclease must first be removed from the reaction system; so products don't continue to be digested. The DNA substrate can be purified by binding to a solid support, which can be accomplished using a purification column or by binding DNA to beads: which are then removed with the DNA. Magnetic beads in particular can facilitate purification by attracting them to a support, then removing the support with the beads and bound DNA or magnetically attracting the magnetic beads to the side or bottom of the well or tube.

At present, heat labile endonucleases are generally used in digestion, and after such use, they are heat inactivated to arrest further digestion. Such heating can affect other reagents in the reaction, or possibly even cause some degree of de-annealing of oligomer strands. Alternative methods of inactivating endonucleases are clearly needed.

SUMMARY

The present invention describes adding an N-terminal Histamine-Maltose Binding Protein ("MBP") tag to an endonuclease to form a fusion protein. The endonuclease is preferably Hind III, a restriction endonuclease. The fusion protein is bound to a solid support, preferably beads, once the enzyme has digested DNA oligomers in solution, in order to arrest further digestion. Preferred beads for binding the tagged enzyme are magnetic beads, which can easily be removed from solution by binding to a support, or can be attracted to accumulate in one region of the reaction mixture (like, the bottom or side of a well or tube). One type of suitable magnetic bead is a nickel bead bound to iminodiacetic acid (IDA) or nitrilotriacetic acid; both of which bind to the histamine portion of the MBP tag.

The invention includes an amino acid sequence at least 80%, 90%, 95%, 98%, or 99% identical to SEQ ID NO: 1 and a DNA sequence encoding it, including a DNA sequence at least 80%, 90%, 95%, 98%, or 99% identical to SEQ ID NO: 2. The histamine portion of the tag can be any histamine-containing sequence including one with six or more histamine residues. Other proteins may be substituted for MBP in the tag, and the tag may be added to other endonucleases besides HindIII.

SEQUENCE LISTING

```
SEQ ID NO.: 1: HindIII-HM fusion protein
DNA sequence:
ATGAAAATCCACCACCACCACCACCACGAAGAAGGTAAACTGGTTATCTG

GATCAACGGTGACAAAGGTTACAACGGTCTGGCGGAAGTTGGTAAAAAAT

TCGAAAAAGACACCGGTATCAAAGTTACCGTTGAACACCCGGACAAACTG

GAAGAAAAATTCCCGCAGGTTGCGGCGACCGGTGACGGTCCGGACATCAT

CTTCTGGGCGCACGACCGTTTCGGTGGTTACGCGCAGTCTGGTCTGCTGG

CGGAAATCACCCCGGACAAAGCGTTCCAGGACAAACTGTACCCGTTCACC

TGGGACGCGGTTCGTTACAACGGTAAACTGATCGCGTACCCGATCGCGGT

TGAAGCGCTGTCTCTGATCTACAACAAAGACCTGCTGCCGAACCCGCCGA

AAACCTGGGAAGAAATCCCGGCGCTGGACAAAGAACTGAAAGCGAAGGT

AAATCTGCGCTGATGTTCAACCTGCAGGAACCGTACTTCACCTGGCCGCT

GATCGCGGCGGACGGTGGTTACGCGTTCAAATACGGTGACATCAAAGACG

TTGGTGTTGACAACGCGGGTGCGAAAGCGGGTCTGACCTTCCTGGTTGAC

CTGATCAAAAACAAACACATGAACGCGGACACCGACTACTCTATCGCGGA

AGCGGCGTTCAACAAAGGTGAAACCGCGATGACCATCAACGGTCCGTGGG

CGTGGTCTAACATCGACACCTCTAAAGTTAACTACGGTGTTACCGTTCTG

CCGACCTTCAAAGGTCAGCCGTCTAAACCGTTCGTTGGTGTTCTGTCTGC

GGGTATCAACGCGGCGTCTCCGAACAAAGAACTGGCGAAAGAATTCCTGG

AAAACTACCTGCTGACCGACGAAGGTCTGGAAGCGGTTAACAAAGACAAA

CCGCTGGGTGCGGTTGCGCTGAAATCTTACGAAGAAGAACTGGCGAAAGA

CCCGCGTATCGCGGCGACCGCGGAAAACGCGGCGAAAGGTGAAATCATGC

CGAACATCCCGCAGATGTCTGCGTTCTGGTACGCGGTTCGTACCGCGGTT

ATCAACGCGGCGTCTGGTCGTCAGACCGTTGACGAAGCGCTGAAAGACGC

GCAGACCAACTCTTCTTCTAACAATAATAACAATAACAATAACAACAACC

TGGGTGAAAACCTGTACTTCCAGGGTATGAAAAAAATCAGCCTTAGAAAAA
```

```
-continued
CTGCTGTCTCTGATCGAAAATCTGACCAATCAAGAGTTTAAACAGGCTAC

CAATAGTCTGATTAGCTTTATCTACAAGCTGAATCGTAATGAGGTCATCG

AACTGGTTCGCAGCATCGGCATCCTGCCGGAAGCTATCAAACCGTCTAGT

ACCCAGGAAAAACTGTTTAGCAAAGCGGGCGATATTGTGCTGGCCAAAGC

CTTTCAGTTACTGAATCTGAATAGCAAACCTCTGGAACAGCGTGGTAATG

CAGGCGATGTGATTGCCCTGTCTAAAGAGTTCAATTATGGCTTAGTTGCG

GATGCCAAATCATTTCGCCTGTCACGCACGGCTAAAAATCAGAAAGATTT

TAAAGTTAAAGCGTTAAGTGAATGGCGCGAAGATAAAGATTATGCGGTGC

TGACCGCACCGTTTTTCCAGTATCCGACGACCAAATCTCAGATTTTTAAA

CAGTCATTAGATGAAAATGTGTTACTGTTTTCATGGGAACATCTGGCCAT

CCTGCTACAACTGGATCTGGAAGAAACCAATATCTTTCCGTTTGAACAGC

TGTGGAATTTTCCTAAAAAACAGTCTAAGAAAACGAGTGTGAGCGATGCC

GAAAACAATTTTATGCGCGATTTTAATAAGTATTTTATGGATCTGTTTAA

AATTGATAAAGATACGCTGAATCAGTTACTGCAAAAAGAAATCAATTTTA

TCGAAGAACGCTCACTGATTGAAAAGAATATTGGAAAAAACAGATCAAT

ATTATCAAAATTTTACACGCGAAGAAGCCATCGAAGCCTTACTGAAAGA

TATTAATATGAGTAGCAAAATCGAAACCATTGATAGCTTTATCAAAGGCA

TCAAATCTAATGATCGCCTGTATCTGTAA

SEQ ID NO.: 2: HindIII-HM fusion protein
sequence (N-terminal His tag is underlined
and the MBP portion is italicized):
MKIHHHHHHEEGKLVIWINGDKGYNGLAEVGKKFEKDTGIKVTVEHPDKL

EEKFPQVAATGDGPDIIFWAHDRFGGYAQSGLLAEITPDKAFQDKLYPFT

WDAVRYNGKLIAYPIAVEALSLIYNKDLLPNPPKTWEEIPALDKELKAKG

KSALMFNLQEPYFTWPLIAADGGYAFKYGDIKDVGVDNAGAKAGLTFLVD

LIKNKHMNADTDYSIAEAAFNKGETAMTINGPWAWSNIDTSKVNYGVTVL

PTFKGQPSKPFVGVLSAGINAASPNKELAKEFLENYLLTDEGLEAVNKDK

PLGAVALKSYEEELAKDPRIAATAENAAKGEIMPNIPQMSAFWYAVRTAV

INAASGRQTVDEALKDAQTNSSSNNNNNNNNNNLGENLYFQGMKKSALEK

LLSLIENLTNQEFKQATNSLISFIYKLNRNEVIELVRSIGILPEAIKPSS

TQEKLFSKAGDIVLAKAFQLLNLNSKPLEQRGNAGDVIALSKEFNYGLVA

DAKSFRLSRTAKNQKDFKVKALSEWREDKDYAVLTAPFFQYPTTKSQIFK

QSLDENVLLFSWEHLAILLQLDLEETNIFPFEQLWNFPKKQSKKTSVSDA

ENNFMRDFNKYFMDLFKIDKDTLNQLLQKEINFIEERSLIEKEYWKKQIN

IIKNFTREEAIEALLKDINMSSKIETIDSFIKGIKSNDRLYL

SEQ ID NO: 3: N-terminal histamine tag: MKIHHHHHH
```

DETAILED DESCRIPTION

The term "magnets," or "magnetic" includes ferromagnetic and paramagnetic materials, including iron, ferric oxide (which can be mixed with a binder), iron alloys, rare earth elements or alloys, ceramic (or ferrite) magnets (made of a sintered composite of powdered iron oxide and barium/strontium carbonate ceramic) and/or an AlNiCo magnet. The alloys can include one or more of: Nd2Fe14B (neodymium), SmCo5, SmCo7, SmFe7, SmCu7 and SmZr7. The magnets materials can include magnetic materials bound to a binding agent, such as nickel-IDA.

The term "beads" includes beads and microbeads, including those made of polyethylene, polyethylene terephthalate, Nylon, polypropylene, polystyrene and polymethyl methacrylate.

The term "magnetic beads" includes bead and microbeads with a magnetic core.

The term "biologically active fragment" refers to any fragment, derivative, homolog or analog of an endonuclease that possesses an in vivo or in vitro activity that is characteristic of that biomolecule. For example, endonucleases can be characterized by biological activities including DNA binding activity and nucleotide digestion activity. A "biologically active fragment" of an endonuclease is any fragment, derivative, homolog or analog that can digest a nucleic acid strand. In some embodiments, the biologically active fragment, derivative, homolog or analog of the mutant HindIII possesses 10%, 20%, 30%, 40%, 50%, 60%, 70%, 75%, 80%, 85%, 90% 95%, or 98% or greater of the biological activity of the endonuclease in an in vivo or in vitro assay such as, for example, DNA binding assays, nucleotide polymerization assays (which may be template-dependent or template-independent), primer extension assays, strand displacement assays, reverse transcriptase assays, proofreading assays, accuracy assays, thermostability assays, ionic stability assays and the like. In some embodiments, a biologically active fragment can include any part of the endonuclease. In some embodiments, the biologically active fragment can optionally include any 25, 50, 75, 100, 150 or more contiguous amino acid residues of the endonuclease. A biologically active fragment of a modified endonuclease can include at least 25 contiguous amino acid residues having at least 80%, 85%, 90%, 95%, 98%, or 99% identity to SEQ ID NO: 2. The invention also includes the polynucleotides encoding any of the foregoing amino acid sequences (which are the coding portions of SEQ ID NO: 1). Biologically active fragments can arise from post transcriptional processing or from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, plant, insect or mammalian cells.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript. In the present invention, it can also refer to changes, deletions, or insertions in the MBP or histamine tag region of the fusion protein.

"Naturally-occurring" or "wild-type" refers to the form found in nature. For example, a naturally occurring or wild-type polypeptide or polynucleotide sequence is a sequence present in an organism, like the HindIII sequence, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

Using the HindIII-HM Protein

In some embodiments, the invention relates to methods (and related kits, systems, apparatuses and compositions) for performing a nucleotide digestion reaction by contacting a HindIII-HM fusion protein or a biologically active fragment thereof with a nucleic acid template. After the digestion has proceeded to specified degree or at a specified time, the fusion protein or biologically active fragment thereof is removed to stop the reaction. A preferred method to remove the fusion protein is using iminodiacetic acid (IDA) or nitrilotriacetic acid (NTA), both of which bind the imidazole rings in the histamine tags. IDA and NTA can be bound to a resin, matrix, bead, or other solid support, whereby removal of the solid support removes the bound fusion protein or biologically active fragment thereof.

In some embodiments, the removal HindIII-HM fusion protein or biologically active fragment thereof can be done using of magnetic beads, including nickel beads, and including nickel beads bound to IDA. The magnetic beads are attracted to a support, such as a magnetic rod inserted into the reaction mixture, and the removal of the magnetic rod removes the HindIII-HM fusion protein or biologically active fragment thereof. Alternatively, attracting the beads and the bound fusion protein to one region of the reaction vessel also arrests the enzyme activity.

In some embodiments, the method can further include detecting a signal indicating the digestion of the DNA oligomer by the HindIII-HM fusion protein or the biologically active fragment thereof using a sensor. In some embodiments, the sensor is an ISFET. In some embodiments, the sensor can include a detectable label or detectable reagent within the polymerizing reaction.

In some embodiments, the method further includes determining the identity of the one or more nucleotides digested by the HindIII-HM fusion protein or the biologically active fragment thereof. In some embodiments, the method further includes determining the number of nucleotides digested by the HindIII-HM fusion protein or the biologically active fragment thereof.

In some embodiments, the invention relates to methods (and related kits, systems, apparatus and compositions) for amplifying nucleic acid fragments following digestion by the HindIII-HM fusion protein or the biologically active fragment thereof, and removal of it. The amplification is preferably done e.g., with a polymerase chain reaction (PCR), emulsion PCR, bridge PCR, an isothermal amplification reaction, recombinase polymerase amplification reaction, proximity ligation amplification, rolling circle amplification or strand displacement amplification. The amplification products can be analyzed thereafter.

In some embodiments, the disclosure generally relates to methods (and related kits, systems, apparatus and compositions) for synthesizing a nucleic acid by incorporating at least one nucleotide onto the end of a primer using a mutant HindIII or a biologically active fragment thereof. Optionally, the method further includes detecting incorporation of the at least one nucleotide onto the end of the primer. In some embodiments, the method further includes determining the identity of at least one of the at least one nucleotide incorporated onto the end of the primer. In some embodiments, the method can include determining the identity of all nucleotides incorporated onto the end of the primer. In some embodiments, the method includes synthesizing the nucleic acid in a template-dependent manner. In some embodiments, the method can include synthesizing the nucleic acid in solution, on a solid support, or in an emulsion (such as emPCR).

Making the Mutant HindIII Restriction Enzyme

In order to provide a HindIII-HM fusion protein or the biologically active fragment thereof which can function in digestion, amino acid substitutions may be at one or more amino acids, 2 or more amino acids, 3 or more amino acids, or more, including where up to 30% of the total number of amino acids of the wild type HindIII sequence are substituted, or where similar substitutions are the fusion protein of SEQ ID NO: 2. Embodiments of the HindIII-HM fusion protein may be anywhere from 70% to 99.99% identical to SEQ ID NO: 2.

The HindIII-HM fusion protein or the biologically active fragment thereof can be expressed in any suitable host system, including a bacterial, yeast, fungal, baculovirus, plant or mammalian host cell.

EXAMPLES

Materials:

Amylose Resin, pUC19, lambda DNA, C2566, 1 kb DNA marker: New England Biolabs, Inc., MA, USA Nickel-IDA magnetic beads: obtained from Beaverbio, Jiangsu, China MBP is often used as a protein solubility partner, or a fusion protein tag, and has an approximate molecular mass of 42.5 kilodaltons.

The N-terminal Histamine tag has the amino acid sequence MKIHHHHHH, SEQ ID NO: 3 (in one embodiment).

The restriction enzyme HindIII is constructed to include an N-terminal His-MBP, having the DNA and protein sequences shown in SEQ ID NOS: 1 and 2, respectively. MBP provides a medium size tag which enables universal tag binding. Including an MBP tag can also help the expression of the restriction enzyme portion of SEQ ID NO: 1.

The N-terminal His-MBP tagged restriction enzyme can be removed from the reaction by binding the His-MBP tag to amylose beads or to other absorbent beads (magnetic or non-magnetic), including nickel beads. The adsorption to the beads deactivates the enzyme. Magnetic beads are preferred as they can be readily removed from the reaction chamber (often, a microtiter plate well or tube) after enzyme binding and deactivation, by attraction to a magnetic or paramagnetic support which is then withdrawn from the reaction chamber, thereby carrying out the beads with it.

In one example, His-MBP tagged HindIII ("HindIII-HM") is constructed with the components in the following order: N-terminal-His tag-MBP-HindIII (see SEQ ID NOS: 1 and 2). SEQ ID NO: 1 is preferably expressed in *E. coli* strain C2566. HindIII-HM can be purified using a conventional FPLC column, or using a nickel bead column followed by purification using an amylose bead column.

Figure 1:
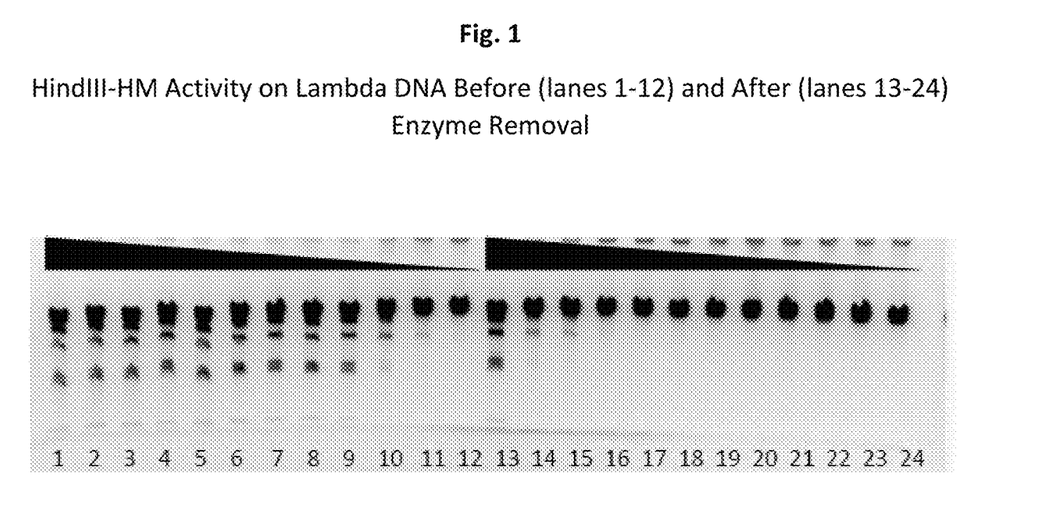
FIG. 1: Activity assay of HindIII-HM (which is: N-terminal-His-MBP-HindIII fusion protein; as shown in SEQ ID NO: 2) on lambda DNA before and after nickel magnetic bead adsorption. A high concentration of HindIII-HM was incubated with nickel-IDA magnetic beads for 1 hour at 4° C. Supernatant was then diluted 2-fold for each successive lane. Lanes 1-12, shows activity of HindIII-HM without bead adsorption, and following gel electrophoretic separation of the reaction products. Lanes 13-24 show the activity of HindIII-HM after bead adsorption, again, following gel electrophoretic separation of the reaction products.

FIG. 1 shows the activity change, starting from high concentrations of HindIII-HM acting on lambda DNA, and before and after adsorption by nickel-IDA magnetic beads. HindIII-HM was incubated with lambda DNA either with or without nickel-IDA magnetic beads at 4° C. for 1 hour. Reaction composition and conditions were: 20 of enzyme, 20 of 10× reaction buffer, 0.4 µl 500 ng/µl lambda DNA, 15.6 µl of water, at 37° C. The reaction buffer was: 50 mM NaCl, 10 mM-Tris-HCl, 10 mM MgCl$_2$, pH 7.9 at 25° C. Moving left to right for lanes 1-12, each successive lane represents an experimental run, where the reaction solution was serially diluted two fold with 50% glycerol for each successive run. The DNA in the supernatant was subject to gel electrophoresis following each run. The same serial dilution was performed on each successive lane for lanes 13 to 24.

Lane 1 to 12 shows results where nickel-IDA magnetic beads were not present. The results show that all of lanes 1-9 show sufficiently high enzyme activity to degrade DNA into the same or similar distinct bands. Lane 13 to 24 shows results where nickel-IDA magnetic beads were in solution. Digestion is complete (evidenced by bands as in lanes 1-9) only in the first lane (No. 13) with the highest enzyme concentration, before any dilution. Therefore, the nickel-magnetic beads adsorbed and deactivated 99.6% of HindIII-HM.

Figure 2:
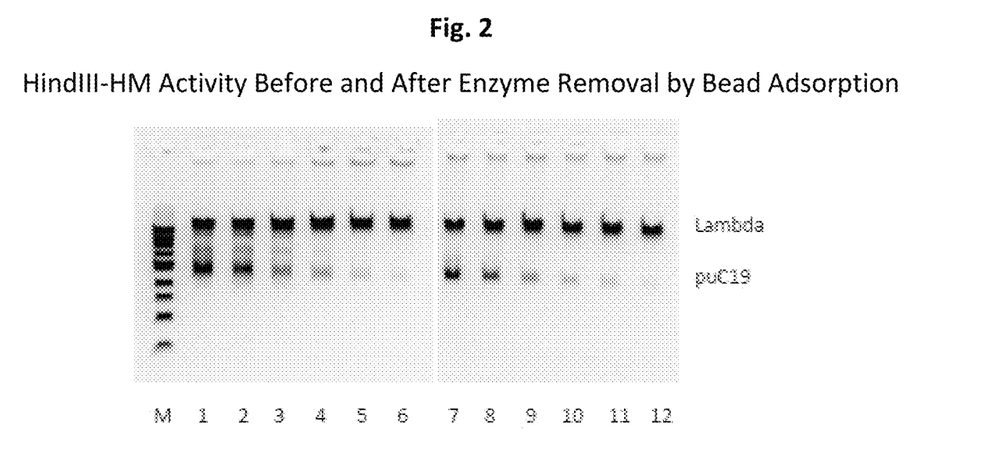
FIG. 2: Activity assay of HindIII-HM remaining in reaction mixture before and after magnetic bead adsorption. Lane M is the 1 kb DNA marker, lanes 1-6 show results following serial twofold dilution (in each lane) of Hind-HM activity without magnetic beads adsorption. Lanes 7-12 show results of digestion by HindIII following magnetic beads adsorption of HindIII-HM and serial twofold dilution (in each lane). In the results shown, pUC19 was run first, then removed by adsorption with nickel magnetic beads which remain in each reaction well. After that, lambda DNA is added to each well and incubated for reaction again, followed by enzyme deactivation by nickel magnetic bead adsorption. Results shown are following electrophoretic separation, where rows are marked showing the degree of pUC19 and lambda DNA digestion by the enzyme into distinct bands.

FIG. 2 shows the activity change after digestion of a first substrate, followed by bead adsorption, then digestion of a different substrate. First, 10 units of HindIII-HM were incubated with 1 µg of the plasmid pUC19 for 1 hour. The reaction buffer was: 50 mM NaCl, 10 mM-Tris-HCl, 10 mM MgCl$_2$, pH 7.9 at 25° C. The reaction composition and conditions were: 2 µl of HindIII-HM (10 units), 2 µl of 10× reaction buffer, 1 µl of 1 µg/ul pUC19, and 15 µl of water at 37° C. for 1 hour.

After reaction, 20 µl of 10% of nickel-IDA magnetic beads were mixed into the reaction mixture, and incubated for 10 minutes. The supernatant was then diluted with 50% glycerol in a twofold serial dilution.

The second step reaction composition was: 2 µl of enzyme, 2 µl of 10× reaction buffer, 0.4 µl 500 ng/µl lambda DNA, and 15.6 µl of water; all incubated for another hour. In FIG. 2, lane M is the 1 kb DNA marker without reaction and following gel separation; lanes 1-6 show results following a twofold serial dilution of HindIII-HM activity, but without magnetic bead presence or adsorption; and lanes 7-12 show the results following a twofold serial dilution of HindIII-HM activity, but with magnetic bead presence and adsorption following reaction.

The results show that in the second step reaction, the enzyme does not digest the lambda DNA at all, meaning, prior adsorption to the nickel-IDA beads (following the step 1 reaction) completely inactivated the enzyme (as shown in lanes 7-12).

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process of inactivating an endonuclease fusion protein with a tag sequence, following a specified quantity or amount of substrate digestion, comprising: providing reaction conditions for a reaction mixture including the fusion protein and a DNA oligomer; allowing a reaction to proceed for a specified period or until a specified quantity of the DNA oligomer has been digested; and terminating the digestion reaction by binding the tag portion of the fusion protein to a solid support, wherein the tag is an N-terminal tag having the amino acid sequence MKIHHHHHH (SEQ ID NO:3).

2. The process of claim 1 wherein the solid support with the bound fusion protein is removed from the reaction mixture or accumulated in a region of the reaction mixture.

3. The process of claim 1 wherein the endonuclease is HindIII or a biologically active fragment thereof.

4. The process of claim 1 wherein the tag further includes a maltose binding protein attached to the C-terminus of SEQ ID NO:3.

5. The process of claim 1 wherein the fusion protein has the amino acid sequence as set forth in SEQ ID NO:2.

6. The process of claim 1 wherein the fusion protein is encoded by the DNA sequence as set forth in SEQ ID NO:1.

7. The process of claim 1 wherein the substrate is lambda DNA or pUC19.

8. The process of claim 1 wherein the solid support is a bead.

9. The process of claim 8 wherein the bead is an agarose bead.

10. The process of claim 8 wherein the bead is magnetic bead.

11. The process of claim 8 wherein the beads are bound to iminodiacetic acid or nitrilotriacetic acid.

12. The process of claim 10 wherein the magnetic bead is nickel or a nickel alloy.

13. The process of claim 10 wherein the magnetic beads are removed from the reaction mixture after binding to the fusion protein or attracted and accumulated in a particular region using magnetic attraction.

14. The process of claim 13 wherein the magnetic beads are removed by attracting them to a magnetic or paramagnetic solid support and removing it from the reaction mixture.

* * * * *